United States Patent [19]
Herzenberg et al.

[11] Patent Number: 5,843,785
[45] Date of Patent: Dec. 1, 1998

[54] GLUTATHIONE DEFICIENCY AS A PROGNOSIS FOR SURVIVAL IN AIDS

[75] Inventors: Leonore A. Herzenberg, Stanford; Stephen C. DeRosa, Palo Alto; Leonard A. Herzenberg, Stanford; Mario Roederer, Redwood City, all of Calif.

[73] Assignee: The Board of Trustees of the Leland Stanford Junior University, Palo Alto, Calif.

[21] Appl. No.: 692,826

[22] Filed: Jul. 25, 1996

[51] Int. Cl.$^6$ ...................................................... G01N 33/49
[52] U.S. Cl. ............................................... 436/86; 436/811
[58] Field of Search ......................... 436/86–90; 530/332

[56] References Cited

PUBLICATIONS

Biosis 92:447496, Abstract only, 1992.
Biosis 91:461805, Abstract only, 1991.
Biosis 90:90496, Abstract only, 1990.

Staal, F.J.T. et al. "Intracellular Glutathione Deficiency in AIDS: Implications for Therapy," *Poster Abstracts*, VIII International Conference on AIDS/III STD World Congress, Amsterdam: the Netherlands, Jul. 19–24, 1992 (Abstract No. PoA 2400), p. A69.

*Primary Examiner*—Lyle A. Alexander
*Attorney, Agent, or Firm*—Flehr Hohbach Test Albrititton & Herbert LLP

[57] ABSTRACT

Glutathione levels are determined using a glutathione surrogate in HIV-positive patients to evaluate survival longevity and determine appropriate treatment. Low glutathione levels indicate a need for a glutathione enhancing supplement and a more aggressive therapeutic regimen, as well as diminishing drugs which may result in the reduction of available glutathione.

7 Claims, 3 Drawing Sheets

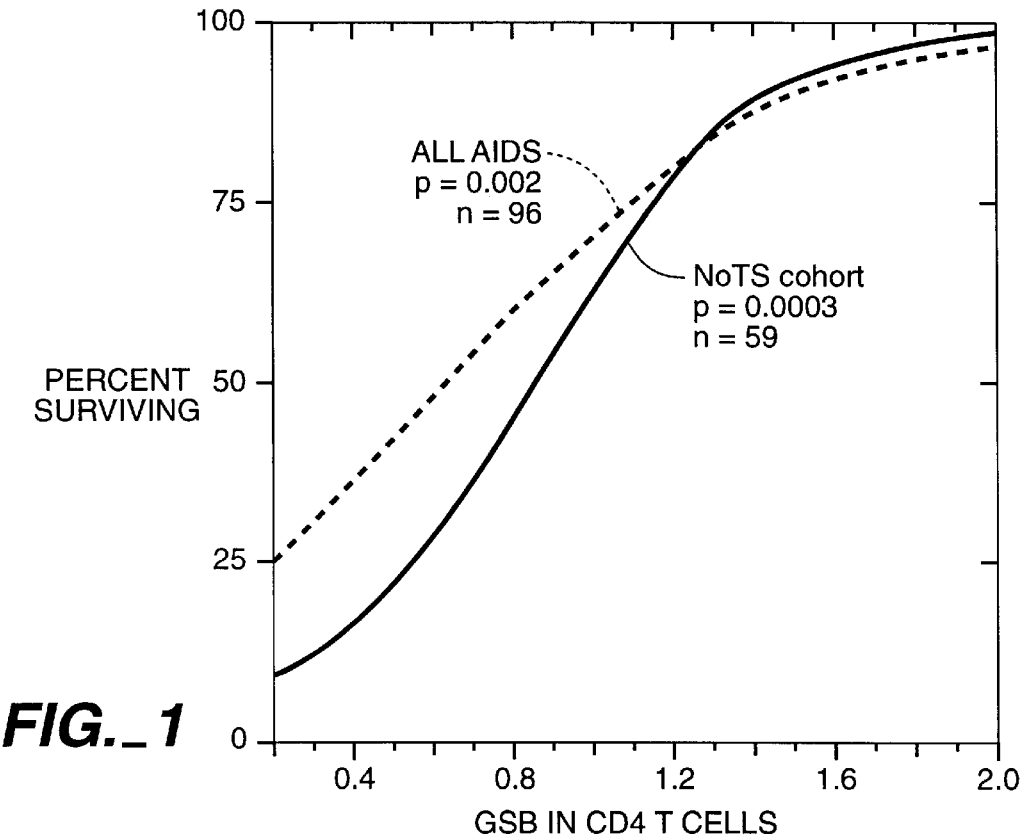
FIG._1
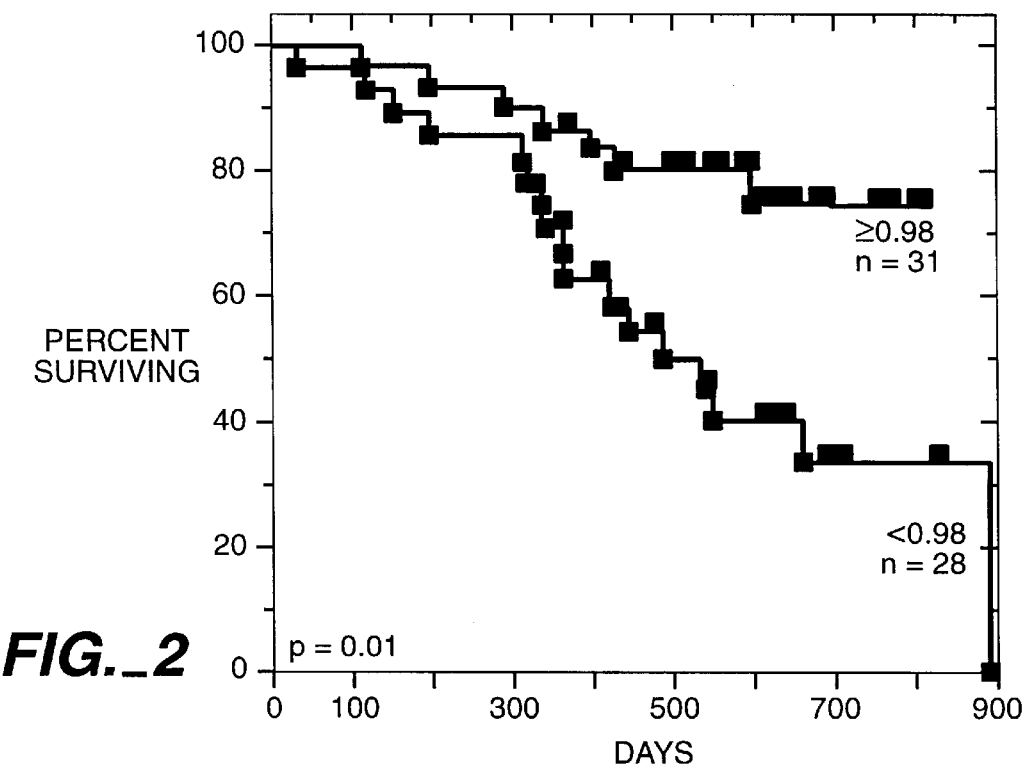
FIG._2

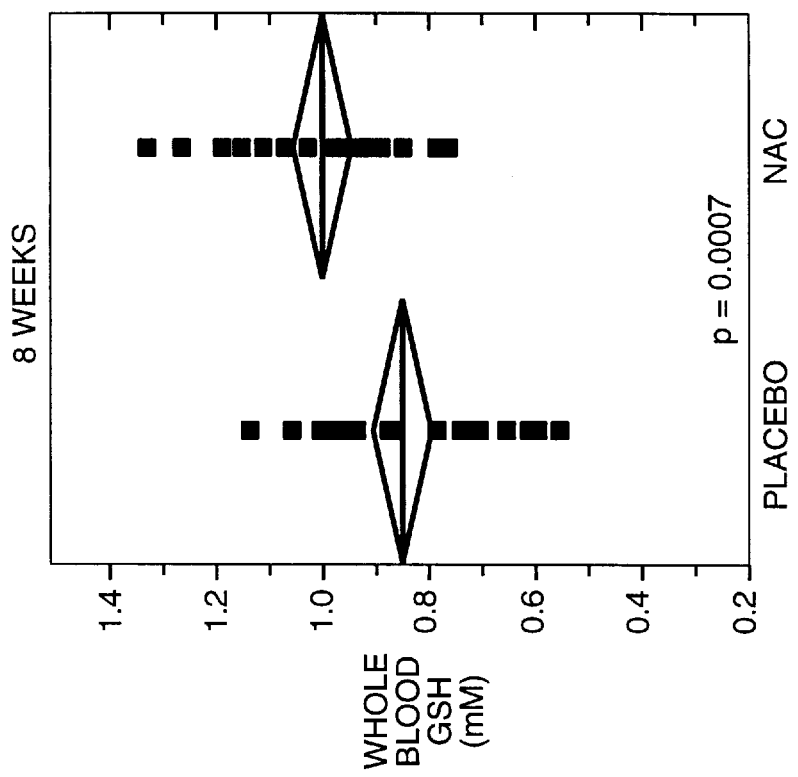
FIG._3B
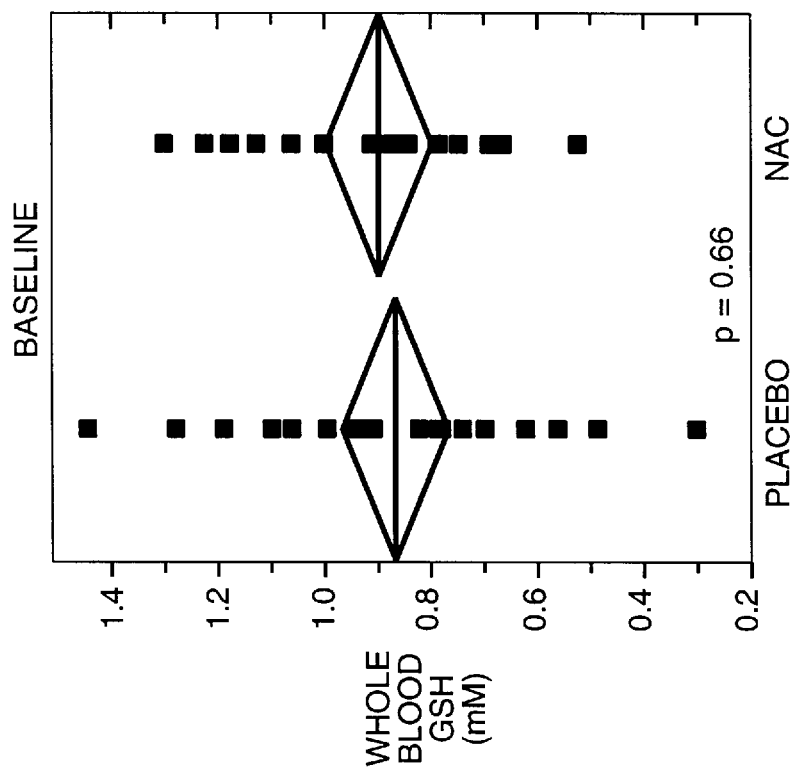
FIG._3A

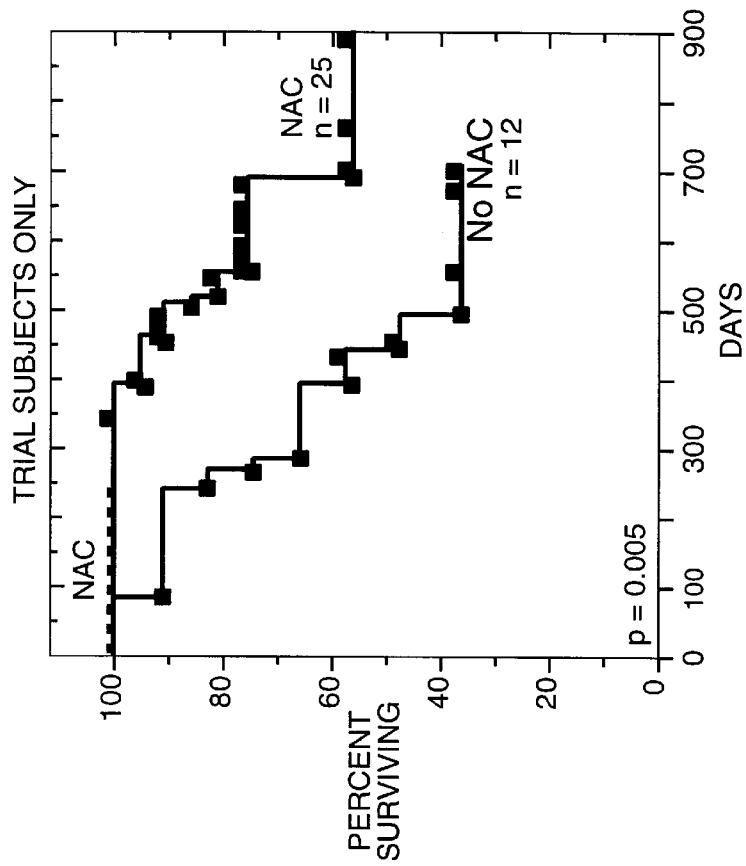
FIG._4B
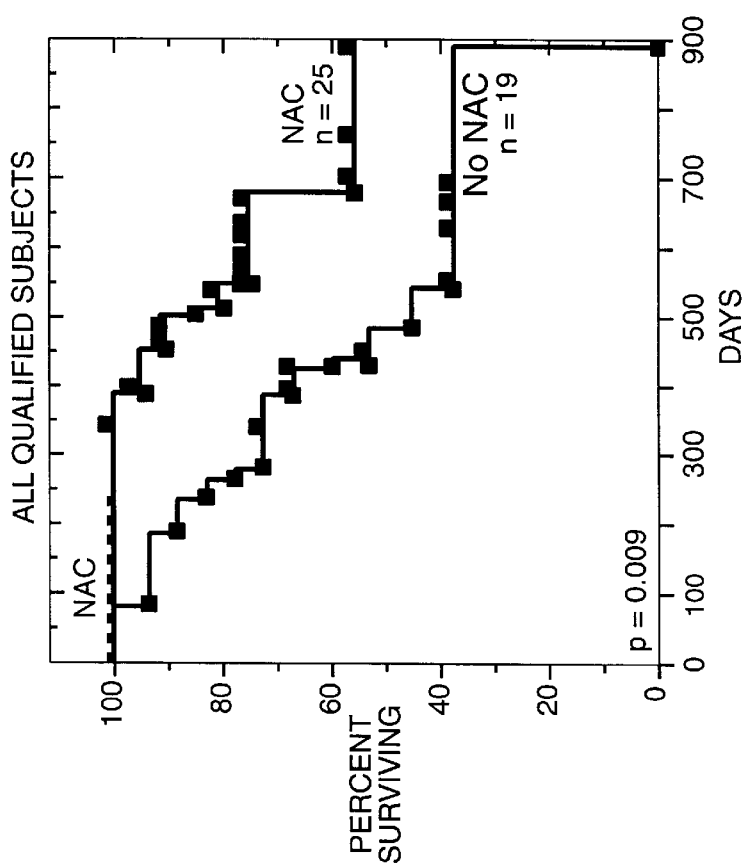
FIG._4A

GLUTATHIONE DEFICIENCY AS A PROGNOSIS FOR SURVIVAL IN AIDS

BACKGROUND

AIDS is an international scourge, which has until recently avoided therapeutic treatments or management. Despite the extensive efforts directed to finding ways to combat HIV, the available targets have been limited. Until recently, the reverse transcriptase has been the primary target. More recently, drugs have become available which are directed against the HIV protease. There is, therefore, greater hope that by using a combination of drugs, the progress of AIDS may be slowed or even stopped.

While these drugs give some hope of extending the lifetime of AIDS patients, these drugs are not without side effects. While their targets are primarily enzymes associated with the HIV virus, these drugs also are able to interact with human enzymes and interfere with their normal function. In order to be able to determine an appropriate regimen for an HIV positive patient, it is of interest to be able to evaluate the status of the patient, in order to determine how aggressive the therapeutic regimen should be. There is, therefore, substantial interest in being able to evaluate the status of an HIV positive patient, as to the ability to respond to the disease, the likely period of survival, and the like.

SUMMARY OF THE INVENTION

Glutathione levels of HIV positive patients are determined, either directly or indirectly, as an indication of the likely period of survival, as well as the need for agents for enhancing the glutathione level. Particularly, the glutathione level of whole blood and/or T cells, particularly helper T cells, is determined as an indication of the period of time for survival and the need for glutathione adjunct treatment.

BRIEF DESCRIPTION OF THE DRAWINGS

Figure Legends

FIG. 1. Probability of surviving for 2–3 years increases with increasing CD4 GSB levels. The solid line shows the logistic regression analysis for survival as a function of CD4 GSB level for what we define as the NoTS (No Trial Subjects) cohort. As indicated in the text, this cohort includes all subjects in our study who had CD4 counts below 200/µl (AIDS), did not have an active OI, and were not enrolled in the NAC trial. The dotted line in the figure shows the analysis for all subjects with AIDS, including those in the NAC trial (most of whom took NAC). Survival status of subjects was determined 2–3 years after baseline data collection. Survival times are computed from the date of the subject's first (screen) visit. At the 95% confidence interval, the regression for the NoTS cohort (solid line) predicts 65±15% survival for individuals at the mean GSB level (0.98) for the NoTS cohort, 50% survival for individuals with GSB levels of 0.85 (0.57–1.0) and less than 25% survival for individuals with GSB levels below 0.6.

FIG. 2: Low CD4 GSB levels are associated with poor survival in AIDS. The Kaplan-Meier analysis for the NoTS cohort (see text and legend for FIG. 1). NoTS subjects are grouped for this analysis according to whether their CD4 GSB levels were above or below the mean GSB level calculated for the cohort. Survival times are computed from the date of the subject's first ("screening") visit. The group of 19 subjects for whom data is shown in the left panel includes all screened subjects who basically qualified for entry into the NAC trial; the subgroup 12 subjects who basically qualified for entry into the NAC trial; the subgroup 12 subjects for whom data is shown in the right panel were actually enrolled in NAC trial (see legend for table 4).

FIGS. 3A and 3B: Oral administration of NAC increases whole blood GSH. Subjects were treated for 8 weeks with orally-administered NAC (n=23) or placebo (n=24) in a randomized, double-blind trial. Subjects took 3200–8000 mg of NAC per day for 8 weeks (median 4400 mg), supplied as 800 mg effervescent tablets by Elan Pharmaceutical Corporation, Gainesville, Ga., who also supplied the placebo. Whole blood GSH was measured by HPLC. Significance was determined by the Anova T-test. The bar in the "means diamond" shows the mean for the group; the points at the top and bottom show the 95% confidence interval. For more extensive statistical analysis, see table 3.

FIGS. 4A and 4B: Taking NAC is associated with increased survival. Kaplan-Meier survival analyses compare subjects who took NAC with similar subjects who did not take NAC. The length of time subjects took NAC ranged from 8–32 weeks (median, 24 weeks; inter-quartile range, 12–27 weeks). Survival times for subjects who took NAC are computed from initiation of NAC ingestion (0 week for NAC arm; 8 weeks after the trial began for placebo arm). Survival times for subjects who did not take NAC are computed from the trial entry or screening date. Log-Rank comparison: p=0.007. Reasons for taking NAC (in the NAC group) or for not taking NAC (in the No-NAC groups) did not significantly influence survival.

DESCRIPTION OF THE SPECIFIC EMBODIMENTS

In accordance with the subject invention, glutathione levels are determined, directly or indirectly, in at least one of whole blood samples or a fraction thereof, such a peripheral blood mononuclear cells ("PBMC"), and helper T cells (CD4$^+$). (In referring to glutathione levels, it is intended to refer to determinations which correlate with the amount of glutathione, but may not provide an accurate determination of the actual amount of glutathione present. Therefore, whenever referring to glutathione levels, it will be understood that it is the value determined by an assay which can be used for comparisons, but does not provide an absolute value.) It is found that glutathione levels, less than about the 50th percentile of GSH ("glutathione"), particularly below the 25th percentile of GSH, as compared to normal controls, have a substantially reduced survival expectancy. By "survival" is intended the longevity expected, that is, the period of time the patient has to live.

The GSH levels may be determined in a variety of ways, particularly using HPLC (Anderson, M. E. Determination of Glutathione and Glutathione Disulfide in Biological Samples. In Meister, A. ed. Methods Enzymol. Vol. 113. Orlando: Academic Press, 1985, 548–555) or by multiparameter fluorescence activated cell sorting ("FACS") analyses to measure intracellular GSH levels, normally in a restricted blood cell population, particularly T-cell subsets in PBMC (Roederrer, M., et al. Disregulation of Leukocyte Glutathione in AIDS. I. Landay, A. L. et al., eds. Clinical Flow Cytometry. Vol. 677. New York, N.Y.: Ann. NY Acad. Sci., 1993: 113–125).

In determining the GSH level in PBMC subsets, particularly T-cells, more particularly helper T-cells, the GSH level is determined indirectly. The cells are reacted with a glutathione derivatizing agent, e.g. monochlorobimane, to form a fluorescent glutathione-S-bimane ("GSB"). Bivariate analyses demonstrate a significant correlation between the FACS measurement of GSH levels (i.e., GSB levels) and HPLC-measured whole blood GSH levels, which mainly reflect GSH levels in erythrocytes. Comparison of CD4 T-cell GSB levels against HPLC-measured whole blood GSH for 47 subjects in a bivariate analysis generates an r value of 0.53 and p value of 0.0001. In at least squares model, CD4 GSB levels significantly predict whole blood GSH; however, the model is greatly improved by including hematocrit level which corrects variation due to the volume of erythrocytes in the blood sample (Adjusted $R^2=0.4$; P=0.004 for CD4 GSB and 0.002 for hematocrit).

By determining the GSH level of HIV-positive patient, one can use the survival probability to determine the nature of the therapy. Of particular interest is the use of a precursor which enhances GSH levels, such as N-acetyl cysteine. See Staal et al., *PNAS USA* (1990) 87:9943–9947; Mihm et al., *AIDS* (1991) 5:497–503; Roederer et al. *PNAS USA* (1990) 87:484–488; Eylar et al. *Cell Mol. Biol.* (1995) 41 (Suppl. I); S35–S40; and Jeanin et al., *J. Exp. Med.* (1995) 182:1785–1792.

In order to determine the GSH levels in particular PBMC subsets, one may use fluorescent conjugated antibodies which are specific for the particular subset. Of particular interest are antibodies specific for CD4, which is a marker for the T helper cell. If total T-cell GSH is to be determined, one may use antibodies to CD3 or other marker associated with T-cells. Various fluorescers may be employed which do not interfere with the fluorescent GSB. Such fluorescers include fluorescein, phycoerythrins, Texas red, allophycocyanins and the like. The particular manner of conjugation is not critical and is well known in the literature.

The blood sample may be harvested in any way, may be citrated, heparinized, or the like, depending upon whether one wishes to use a whole blood sample or determine only a blood cell subset.

The following samples are offered by way of illustration and not by way of limitation.

EXPERIMENTAL

Methods

A. GSH Measurements

We used HPLC analyses to measure GSH levels in rapidly processed whole blood samples and multiparameter Fluorescence Activated Cell Sorter (FACS) analyses to measure intracellular GSH levels in T cell subsets in peripheral blood mononuclear cells (PBMC) reacted with monochlorobiomane to form the fluorescent glutathione-S-bimane (GSB) conjugate. We determined the median GSB level for each PBMC subset for each subject and used these median values in subsequent analyses, e.g., to compute means for groups of subjects, to display distributions, to group subjects, etc. GSB levels are expressed relative to the lymphocyte GSB level in a frozen PBMC standard measured in parallel with the PBMC samples.

Bivariate analyses demonstrate a significant correlation between the FACS measurements of GSH levels (i.e., GSB levels) and HPLC-measured whole blood GSH levels, which mainly reflect GSH levels in erythrocytes. For example, comparison of CD4 T cell GSB levels against HPLC-measured whole blood GSH for 47 subjects in a bivariate analysis generates an r value of 0.53 and p value of 0.0001. In a least squares model, CD4 GSB levels significantly predicts whole blood GSH; however, the model is greatly improved by including hematocrit level, which corrects for variation due to the volume of erythrocytes in the blood sample (Adjusted $R^2=0.4$; p=0.004 for CD4 GSB and 0.002 for hematocrit).

B. Survival Analyses: Relationship to GSB Levels

We collected baseline data, including GSH levels, T cell subset counts and clinical laboratory measurements for over 200 HIV-infected subjects, 83 of whom were enrolled into a double-blind, placebo-controlled trial testing the functional bioavailability of NAC. Two to three years later, we surveyed the survival status of all subjects and evaluated the relationships between survival and GSH levels. Since all but 2 of the deaths we recorded occurred in subjects with a diagnosis of AIDS (defined as having CD4 T cell counts below $200/\mu l$), we restricted analysis to the 96 subjects in this group and to a subgroup of 59 subjects not enrolled in the NAC trial (NoTS cohort).

C. GSH Replenishment Following Oral Administration of NAC

Subjects were enrolled in a randomized, double-blind, placebo-controlled trial and given either NAC (4800 mg/day on average) or placebo for 8 weeks. All subjects who qualified for enrollment had low GSB levels, were free of active opportunistic infections and were otherwise relatively healthy, as judged by Karnofsky score and professional assessment. Subjects were also required to have maintained a stable reverse-transcriptase inhibitor regimen for the previous four months and were limited with respect to the taking of drugs that deplete GSH (e.g., acetaminophen) or diminish oxidative stress (e.g., high doses of vitamin C or E).

D. Survival Analyses: Relationship to NAC Administration

Subjects were given NAC either because they were randomized to the NAC arm of the GSH replenishment trial or because they elected to take open-label NAC during the continuation phase of the trial. Since the open-label option prevented maintenance of the placebo control for the survival study, we used statistical methods to evaluate potential bias introduced by selecting the control group from subjects who qualified for the trial but were not given NAC (e.g., declined to enter the trial) or were given NAC only for a very short period (e.g., chose to leave the trial for reasons other than illness).

E. Statistical Analyses

We used the JMP Macintosh statistical package produced by the SAS Institute (Carey, N.C.) for all statistical analyses.

Results

A. Survival is Dramatically Lower in Subjects with Low CD4 T cell GSH Levels

CD4 T cell GSH levels, referred to hereafter simply as GSB levels, tend to be lower in subjects with AIDS (defined for this study as subjects with CD4 T cell counts below $200/\mu l$) (Table 1). The mean GSB level for these subjects is below the GSB levels observed in over 80 percent of uninfected control subjects. In addition, because trial enrollment criteria so specified, GSB levels for subjects with AIDS who qualified for the NAC trial were substantially lower than the group with AIDS as a whole. Nearly all were below the 25th percentile GSB level for controls.

Roughly forty percent (37/96) of the subjects with AIDS in our study died within 2–3 years of baseline data collection. The great majority of these deaths occurred among subjects with GSB levels below the mean for the group as a whole; very few deaths occurred among subjects with the highest GSB levels. The logistic regression analysis in FIG. 1 shows this sharp differential in survival between subjects with low and high GSB levels. The two curves in the figure show data for all subjects with AIDS in our study (dashed curve) and for those subjects who were not enrolled in the NAC trial (solid curve). The difference between these two curves reflects the lower GSB levels in the trial subjects and the strikingly better survival of these subjects despite their lower initial GSB levels. Studies discussed below show that the majority of subjects in the trial took NAC, and that the increased survival is associated with taking NAC for more than 8 weeks.

To examine the influence of GSB levels on survival without the confounding influence of NAC, we restricted our analysis to those subjects with AIDS who were not enrolled in the NAC trial. The solid curve in FIG. 1 is based on data from these subjects, whom we refer to as the NoTS (No Trial Subjects) cohort. All subjects enrolled in the NAC trial, regardless of whether they took NAC, are excluded from this cohort; all subjects with AIDS other than those in the trial are included.

As with the overall cohort, most of the deaths in the NoTS cohort are concentrated among subjects with the lowest GSB levels. In essence, only 27 percent of subjects in the lowest quartile of the GSB distribution survived the 2–3 year observation period of this study whereas 87 percent of those in the highest quartile survived. The (solid) logistic regression curve in FIG. 1 shows the significant increase in the probability of surviving for NoTS subjects with progressively higher baseline GSB levels.

Logistic regression analyses demonstrate the importance of baseline GSB levels for survival by reporting the effect of baseline GSB levels on the survival status of subjects 2–3 years after baseline data collection. Kaplan-Meier analyses, which report survival as a function of time for subjects grouped according to GSB level (above or below the mean for the NoTS cohort), similarly show that higher GSB levels are associated with longer survival. Finally, proportional hazard analysis (Table 2), which take both survival time, and baseline GSB levels into account, show that GSB levels predict survival for subjects in the NoTS cohort and report a 2-fold increase in survival for a difference of 0.3 GSB units (the standard deviation of the GSB levels in the NoTS cohort). CD4 T cell counts also show a significant ability to predict survival for NoTS subjects; however, this significance is lost when GSB levels are added to the model (table 2). Since CD4 T cell counts are loosely correlated with GSB levels, this loss of significance suggests that the GSB levels, rather than CD4 T cell counts, underlie the ability of CD4 T cell counts to predict survival in subjects with AIDS (particularly among subjects such as those in the NoTS cohort, who were initially screened to eliminate subjects with life-threatening conditions). Thus, GSB levels may actually constitute a better predictor of survival than CD4 T cell counts for relatively healthy subjects with CD4 T cell counts below 200 $\mu l$.

Aside from their intrinsic interest with respect to mechanisms involved in the pathogenesis of HIV disease, these findings are important in terms of providing a more accurate prediction of survival for a group of subjects that is poorly served by the present methods. In addition, these findings provide a means for subject selection or data evaluation in clinical trials aimed at slowing passage through the latter stages of HIV disease. In essence, we have shown that low GSB levels (an index of GSH depletion and oxidative stress) identify a high-risk subgroup of subjects with AIDS, only a small percentage of whom are likely to survive longer than 2 years in the absence of intervention.

B. Oral Administration of NAC Replenishes GSH, Particularly in Individuals with Low GSH Levels Data from the randomized, double-blind, placebo-controlled trial that we conducted show that administration of NAC at 4400 mg per day for 8 weeks significantly elevates whole blood GSH and GSH in T lymphocytes. FIG. 3 presents a simplified view: no significant difference in whole blood GSH levels in placebo and NAC treatment groups at the start of the trial; significantly higher GSH levels in subjects in the NAC arm after 8 weeks of treatment. Table 3 shows data from covariate analyses demonstrating that NAC increases whole blood GSH levels more effectively in the subjects who had the lowest GSB levels at the start of the trial. Additional analyses (not shown) similarly demonstrate that NAC increases CD4 T cell and CD8 T cell GSB levels, particularly in subjects whose initial GSB levels were low. Thus, as might be expected, NAC is most effective in raising GSH (and GSB) levels when those levels are substantially depleted.

C. NAC Ingestion is Associated with a Substantial Improvement of Survival in Subjects with AIDS The NAC trial discussed above was not designed to test NAC efficacy in prolonging survival. However, after the initial double-blind placebo-controlled phase of the trial (8 weeks duration), all subjects were offered open-label NAC for up to 6 months during the continuation phase of the trial. As part of our overall monitoring study, we examined the fate of these subjects over the next 2–3 years. To our surprise, given the relatively short time (8–32 weeks) that NAC was administered, we found that NAC ingestion was associated with substantially longer survival.

As indicated, the protocol for the NAC trial precluded controlled evaluation of the effect of NAC on survival of the subjects in the trial. All trial subjects were offered open-label NAC and most took advantage of this opportunity. However, we had complete baseline (screening) data and monitoring information for a number of subjects who were comparable to those who took NAC in this study: 3 completed the placebo arm but declined the open-label NAC; 9 left the trial for reasons other than illness and either did not take NAC at all or took it for a very short time (mainly <1 week); another 5 qualified for the trial but chose not to enter; and an additional 2 were disqualified only because of recent changes in their reverse-transcriptase inhibitor regimen. Thus, although we lacked a proper placebo control group for survival comparison, we had a total of 19 subjects who did not take NAC but whose history indicated that they were highly similar to those who did. We confirmed the comparability of these two groups (NAC and "NoNAC" groups) in analyses that failed to reveal any significant differences between them for a wide variety of clinical and FACS measurements, including GSB levels and CD4 T cell counts (see legend for table 4).

Since the enrollment criteria for the trial specifically excluded subjects with higher GSB levels, GSB levels in subjects in the NAC and NoNAC groups were amongst the lowest in the study. Therefore, based on data presented above (FIGS. 1 and 2), the probability that these subjects would survive the 2–3 year observation period in our study was very low. Consistent with this, 11 of the 19 subjects in the NoNAC group died before the end of the observation period. In contrast, however, only 6 of the 25 subjects in the NAC group succumbed. Furthermore, half of the deaths in the NoNAC group occurred before the first death in the NAC group.

TABLE 1

CD4 GSB levels are lower in subjects with AIDS

| Subjects* | | n≠ | CD4 GSB‡ (Mean ± SD) |
|---|---|---|---|
| Uninfected | | 47 | 1.14 ± 0.28 |
| All HIV → | | 203 | 0.97 ± 0.28 |
| CD4 > 200 | All | 107 | 1.05 ± 0.25 |
| CD4 ≦ 200 | All | 96 | 0.88 ± 0.29 |
| (AIDS) | NoTS cohort§ | 59 | 0.98 ± 0.31 |
|  | Trial subjects¶ | 37 | 0.72 ± 0.16 |

*Groups of subjects studied. CD4 ≦ 200 = subjects with CD4 T-cell counts less than or equal to 200/µl, used in this study as synonymous with subjects with AIDS. Percentage of survivors at the end of the 2–3 year observation period: CD4 > 200 = 97%; CD4 ≦ 200 = 65%.
≠Number of subjects for whom CD4 GSB, absolute CD4 T-cell counts and survival status were recorded and computations are based. Overall study group composition: total, 203; male, 194; Caucasian, 151; mean age, 40.4 ± 7.8, range 23–68.
‡CD4 GSB values were normally distributed for all groups and differed significantly for all combinations of distinct groups (Anova T-test); $p \leq 0.0001$ for uninfected vs. all HIV*, CD4 > 200 vs CD4 ≦ 200 and NoTS vs Trial subjects; p = 0.002 for NoTS vs CD4 > 200. Standard error of the mean (SEM) for CD4 GSB means for the groups shown = 0.02–0.04. SD = standard deviation.
§NoTS cohort = all subjects with AIDS who were not enrolled into the NAC trial.
¶Trial subject group includes all NAC and placebo arm subjects with CD4 T-cell counts below 200/µl (37/55 in the trial as a whole). Low CD4 GSB levels for these subjects reflect the trial enrollment requirement for low GSB levels.

TABLE 2

CD4 GSB levels predict survival better than CD4 T-cell counts in subjects with AIDS

| Variables entered into the model | Risk ratio (NoTS cohort, n = 59)* | p value ↑ |
|---|---|---|
| CD4 GSB | 2.1 (1.4–3.4) | 0.0008 |
| CD4 T-cell count | 1.2 (1.0–1.4)‡ | 0.018 |
| CD4 T cell count | ns§ | 0.3 (ns) |
| CD4 GSB | 1.9 (1.2–3.2) | 0.009 |

*Proportional hazard analysis of survival of the NoTS cohort (CD4 T-cell counts below 200/µl; no trial subjects); CD4 GSB is also a significant predictor when computed with hematocrit and CD4 T-cell count in the model.
≠Effect likelihood calculated for the indicated variables, adjusted for others in the model if it contains more than one variable.
‡Risk ratio = change in probability of suviving per unit defined as follows: CD4 T-cell count, per 20 T-cells; GSB, per 0.31 GSB units (standard deviation calculated for NoTS cohort); 95% confidence limits are shown in parentheses.
§Not significant. In essence the change to 'not significant' when CD4 GSB is included in the computation suggests that the relationship between CD4 count and survival actually reflects the loose correlation between CD4 count and CD4 GSB level and the closer relationship of CD4 GSB levels to survival.

TABLE 3

NAC-dependent increase in whole blood GSH

| Combination of variables tested | Contribution to prediction of whole blood GSH levels at the end of an 8 week trial* | | |
|---|---|---|---|
| | p value | R²≠ | RMSE‡ |
| 0 week GSH | <0.0001 | 0.49 | 0.12 |
| NAC vs Placebo | 0.0001 | | |
| 0 week GSH | 0.0004 | | |
| NAC vs Placebo | <0.0001 | 0.56 | 0.11 |
| 0 week CD4 GSB§ | 0.008 | | |

*Whole blood GSH principally reports GSH levels in erythrocytes in blood. Blood samples from 47 subjects were tested at the beginning and end of an 8 week randomized double-lined placebo-controled trial testing the ability of orally-administere NAC to raise GSH. Data show the standard least squares model fit. Subjects took 3200—8000 mg of NAC per day (median 4400 mg) for up to 8 months, supplied as 800 mg effervescent tables.
≠R² adjusted for number of variables added.
‡Root mean square error.
§The significant contribution of initial CD4 GSB values, which are loosely correlated with initial whole blood GSH levels, reflects the tendency for NAC ingestion to result in a greater increase in GSH levels in subjects with low initial GSB values.

TABLE 4

Taking NAC is associated with better survival

| NAC history of subjects* | n≠ | Survival at 2.5 years‡ (Percent) | CD4 GSB (Mean at baseline)§ |
|---|---|---|---|
| NAC (8–32 weeks) | 25 | 76 | 0.73 |
| No NAC (matched to NAC group)¶ | 19 | 42 | 0.72 |

*All subjects had CD4 T-Cell counts below 200/µl and GSB levels low enough to qualify for entry into the NAC trial (Dubs et al, in preparation). All subjects who took NAC were enrolled in the NAC trial. NAC subjects took NAC for 8–32 weeks. Some were randomized to the NAC arm of the trial; other to open-label NAC during the continuation phase.
≠Number of subjects in each group.
‡Proportional hazard calculation for NAC; No-NAC survival yields a survival risk ratio of 1.9 (1.1–3.2, 95% confidence interval), p = 0.013. Survival time in the model is computed from the time each subject began taking NAC. Table shows percentage surviving at the end of the 2.5 year observation period. Kaplan-Meier analyses comparing survival in the NAC and No-NAC groups is shown in FIG. 4.
§Standard deviations for mean CD4 GSB range from 0.14–0.17.
¶There were no significant differences (p > 0.1) in baseline measurements between the NAC and the No-NAC group for all parameters tested, including the following: absolute CD4 and CD8 counts; naive and memory T-cell subset counts; hematocrit and other clinical laboratory tests; Karnofsky score; age; weight; GSB levels in B cells, monocytes, NK cells and all T-cell subsets.

It is evident from the above results, that by determining GSH levels in a HIV-positive patient, one can evaluate the survival probability as well as the need for particular therapies. Particularly, N-acetyl cysteine treatment can be initiated, and the degree of aggressiveness of other drug treatments evaluated. In this manner, AIDS treatment therapies can be developed.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed:

1. A method for evaluating the probability of an HIV positive patient surviving over two to three years following the evaluation, said method comprising:

determining the glutathione level, directly or indirectly, in the blood cells of said patient or a fraction thereof, wherein a reduced glutathione level as compared to an average level in HIV negative humans is indicative of a reduced probability of survival in comparison to HIV negative humans.

2. A method according to claim 1, wherein said determining is by FACS.

3. A method according to claim 1, wherein said determining is by HPLC.

4. A method according to claim 1, wherein said fraction is the PBMC or helper T cell fraction.

5. A method for evaluating the probability of survival of an HIV positive patient over two to three years following the evaluation, said method comprising:

contacting cells from whole blood with a glutathione derivatizing agent to produce a fluorescent conjugate;

determining the amount of said fluorescent conjugate as indicative of the glutathione level in the blood cells of said patient or a fraction thereof by measuring the fluorescence of said sample;

wherein a reduced glutathione level as compared to an average level in HIV negative humans is indicative of a reduced probability of survival in comparison to HIV negative humans.

6. A method according to claim 5, wherein said derivatizing agent is monochlorobimane and said measuring is by means of FACS.

7. A method according to claim 5, wherein said cells CD4+ cells.

* * * * *

UNITED STATES PATENT AND TRADEMARK OFFICE
CERTIFICATE OF CORRECTION

PATENT NO. : 5,843,785
DATED : December 1, 1998
INVENTOR(S) : HERZENBERG et al.

It is certified that error appears in the above-indentified patent and that said Letters Patent is hereby corrected as shown below:

Column 4, line 44, of the Experimental delete "N.C." and insert --NC--.

Column 8, line 14, of Table 3, delete "orally-administere" and insert --orally-administered--.

Signed and Sealed this

Tenth Day of August, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO. : 5,843,785
DATED : December 1, 1998
INVENTOR(S) : HERSENBER, et al.

It is certified that error appears in the above-indentified patent and that said Letters Patent is hereby corrected as shown below:

Column 1, line 3, immediately preceding BACKGROUND OF THE INVENTION, insert a new paragraph to read --This invention was made with Government support under Grant No.: CA 42509 awarded by the National Institutes of Health. The Government has certain rights in this invention.--

Signed and Sealed this

Fourth Day of January, 2000

Attest:

Attesting Officer

Acting Commissioner of Patents and Trademarks